United States Patent
Sakuma et al.

(10) Patent No.: US 9,829,462 B2
(45) Date of Patent: Nov. 28, 2017

(54) GAS SENSOR ELEMENT AND GAS SENSOR (71) Applicant: NGK SPARK PLUG CO., LTD., Nagoya-shi, Aichi (JP)

(72) Inventors: Syun Sakuma, Inuyama (JP); Masaki Onkawa, Konan (JP); Yuta Oishi, Niwa-gun (JP); Nobuo Furuta, Kasugai (JP); Masaki Mizutani, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 1 day.

(21) Appl. No.: 14/833,634

(22) Filed: Aug. 24, 2015

(65) Prior Publication Data
US 2016/0054256 A1 Feb. 25, 2016

(30) Foreign Application Priority Data

Aug. 25, 2014 (JP) .................................. 2014-170423
Jul. 10, 2015 (JP) .................................. 2015-138653

(51) Int. Cl.
G01N 27/407 (2006.01)
(52) U.S. Cl.
CPC ................................ G01N 27/4071 (2013.01)
(58) Field of Classification Search
CPC ......................................... G01N 27/406–27/41
See application file for complete search history.

(56) References Cited

U.S. PATENT DOCUMENTS

| 2001/0017057 A1* | 8/2001 | Fukaya | F02D 35/023 73/204.11 |
| 2008/0060941 A1* | 3/2008 | Ieda | G01N 27/4065 204/431 |
| 2011/0220496 A1* | 9/2011 | Oya | G01N 27/407 204/424 |
| 2012/0234697 A1* | 9/2012 | Onogi | G01N 27/4074 205/775 |
| 2013/0032480 A1* | 2/2013 | Ito | G01N 27/406 204/424 |

FOREIGN PATENT DOCUMENTS

JP 2012-173146 A 9/2012
JP 201-3050440 A1 * 3/2013

* cited by examiner

*Primary Examiner* — J. Christopher Ball
(74) *Attorney, Agent, or Firm* — Stites & Harbison, PLLC; Jeffrey A. Haeberlin; James R. Hayne (57) ABSTRACT

A gas sensor element includes a laminate formed of a detecting element section and a heater section, and a porous protection layer covering a forward end portion of the laminate. The detecting element section has one or more cells having a solid electrolyte body and a pair of electrodes. The heater section has a heater. Side surfaces of the solid electrolyte bodies in parallel with the direction of lamination are covered with dense insulating members. The cell-to-be-controlled is temperature controlled by the heater to 600° C. to 830° C. The porous protection layer is formed on the laminate from a forward end portion to a region which has a temperature of 500° C. or higher when the temperature control is performed, and the porous protection layer is not formed in a region which has a temperature of 300° C. or lower when the temperature control is performed.

6 Claims, 4 Drawing Sheets

GAS SENSOR ELEMENT AND GAS SENSOR

CROSS REFERENCE TO RELATED APPLICATIONS

The present application claims priority to Japanese Patent Application No. 2015-138653, which was filed on Jul. 10, 2015, and Japanese Patent Application No. 2014-170423, which was filed on Aug. 25, 2014, the disclosures of which are herein incorporated by reference in their entirety.

BACKGROUND OF THE INVENTION

Field of the Invention

The present invention relates to a gas sensor element and a gas sensor used preferably for detecting the concentration of a particular gas contained in, for example, combustion gas or exhaust gas of a combustor, an internal combustion engine, etc.

Description of Related Art

Figure 6:
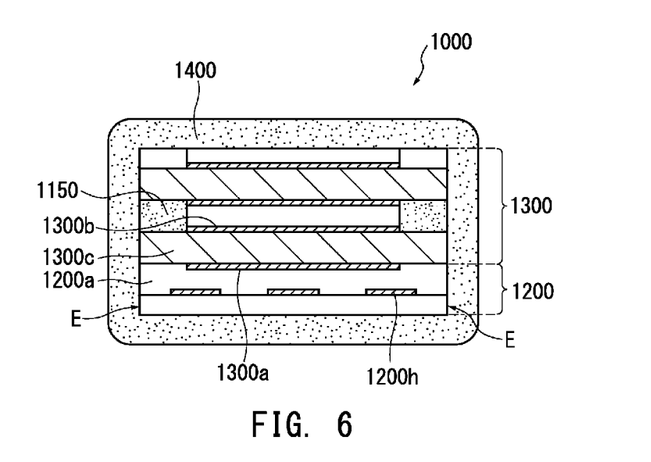
FIG. 6 is a schematic sectional view of a conventional gas sensor element taken orthogonally to the axial direction.

Conventionally, a gas sensor is used for detecting the concentration of a particular component (oxygen, etc.) in exhaust gas of an internal combustion engine. As shown in FIG. 6, this gas sensor has a gas sensor element 1000 provided therein. The gas sensor element 1000 includes a laminate of a detecting element section 1300 and a heater section 1200. The detecting element section 1300 has a cell composed of a solid electrolyte body 1300c, and a pair of electrodes 1300a and 1300b disposed on the solid electrolyte body 1300c. The heater section 1200 is configured such that a heater 1200h is provided in an insulator and generates heat through application of electricity thereto. Heat generated by the heater 1200h activates the solid electrolyte body 1300c, whereby detection by the gas sensor element 1000 is enabled.

Meanwhile, the gas sensor element 1000 may be exposed to poisoning substances, such as silicon and phosphorus, contained in exhaust gas and may suffer adhesion of water droplets contained in exhaust gas. Thus, in order to trap poisoning substances and to prevent direct contact of water droplets with the gas sensor element 1000, the outer surface of the gas sensor element 1000 is covered with a porous protection layer 1400. That is, in the laminate, a forward end portion to be exposed to gas to be measured (exhaust gas) is entirely covered with the porous protection layer 1400 (refer to Patent Document 1). Conventionally, the porous protection layer 1400 is formed on a forward end portion of the gas sensor element 1000 at least in the entire region which has a temperature of 200° C. or higher in the course of use.

RELATED ART DOCUMENTS

Patent Document 1 is Japanese Patent Application Laid-Open (kokai) No. 2012-173146.

BRIEF SUMMARY OF THE INVENTION

However, when the porous protection layer 1400 is provided at a forward end portion of the gas sensor element 1000, heat capacity of the porous protection layer 1400 and, in turn, heat capacity of the entire gas sensor element 1000, increases, thereby raising the problem of an increase in power consumption in heating the gas sensor element 1000 by the heater 1200h and an increase in standby time until initiation of detection.

Meanwhile, by means of the porous protection layer 1400 being formed only at a further forward high-temperature end portion of the gas sensor element 1000 which has a temperature in excess of 200° C., the area of formation of the porous protection layer 1400 is reduced, whereby the above-mentioned heat capacity can be reduced.

However, in the general gas sensor element 1000, as mentioned above, the plate-like solid electrolyte body 1300c is laminated with various insulating layers 1200a, etc., of alumina or the like, and the end surfaces (surfaces E in FIG. 6) of the solid electrolyte body 1300c and the insulating layer 1200a are exposed to the exterior of the gas sensor element 1000. Since the solid electrolyte body 1300c is higher in thermal expansion coefficient than the insulating layer 1200a, if a water droplet comes into contact with (adheres to) a high-temperature portion of an end surface of the gas sensor element 1000, cracking may occur as a result of imposition of thermal stress on the solid electrolyte body 1300c.

Therefore, a region of the gas sensor element 1000 where direct adhesion of water to the solid electrolyte body 1300c does not generate excessive thermal stress; i.e., a region which has a temperature of less than 200° C. in the course of use, does not need to be covered with the porous protection layer 1400; however, since a region which has a temperature of 200° C. or higher in the course of use has no choice but to be covered with the porous protection layer 1400, a reduction in heat capacity has not been achieved.

Thus, an object of the present invention is to provide a gas sensor element and a gas sensor which exhibit a reduction in power consumption in heating the gas sensor element having a porous protection layer by a heater and a reduction in standby time until initiation of detection and which restrain occurrence of cracking as a result of adhesion of water to a solid electrolyte body.

In order to achieve the above object, a gas sensor element of the present invention comprises a laminate which extends in a longitudinal direction and is formed by laminating a detecting element section and a heater section together, and a porous protection layer which covers a forward end portion of the laminate to be exposed to gas to be measured. The detecting element section has one or more cells each having a solid electrolyte body and a pair of electrodes disposed on the solid electrolyte body. The heater section has a heater provided in an insulator and adapted to generate heat through application of electricity thereto. In the gas sensor element, all end surfaces (i.e., side surfaces) of the solid electrolyte body in parallel with a direction of lamination are covered with a dense insulating member. Of the cells, a cell-to-be-controlled is subjected to temperature control by means of the heater, and a target control temperature thereof is 600° C. to 830° C. The porous protection layer is formed on the laminate so as to extend from a forward end portion of the gas sensor element to a region which has a temperature of 500° C. or higher when the temperature control by means of the heater is performed (i.e., a region having an operating temperature of 500° C. or higher), and the porous protection layer is not formed in a region which has a temperature of 300° C. or lower when the temperature control is performed (i.e., a region having an operating temperature of 300° C. or lower).

According to this gas sensor element, all end surfaces of the solid electrolyte body are covered with the dense insulating member. Accordingly, the end surfaces are not exposed to the exterior of the gas sensor element. Thus, even when a water droplet comes into direct contact with (adheres to) a region of the gas sensor element which has a temperature in excess of 200° C. and equal to or less than 300° C., excessive thermal stress is not imposed on the solid electrolyte body, thereby restraining occurrence of cracking.

Therefore, by means of the porous protection layer being formed at least in a higher-temperature region which is to have a temperature of 500° C. or higher, and being not formed in a region which is to have a temperature of 300° C. or less, as compared with the conventional gas sensor element having the porous protection layer formed in a region which is to have a temperature of 200° C. or higher, the area of formation of the porous protection layer can be reduced, and the porous protection layer and, in turn, the gas sensor element can be reduced in heat capacity. As a result, power consumption in heating the gas sensor element by the heater and standby time until initiation of detection can be reduced.

In the gas sensor element of the present invention, the porous protection layer is not necessarily formed on the laminate in a region which has a temperature of less than 500° C. when the temperature control by means of the heater is performed (i.e., a region having an operating temperature of less than 500° C.).

According to this gas sensor element, since the area of formation of the porous protection layer can be further reduced to such an extent as not to cause occurrence of cracking, heat capacity of the porous protection layer and, in turn, heat capacity of the gas sensor element, is reduced, thereby further reducing power consumption, along with standby time until initiation of detection.

In the gas sensor element of the present invention, the porous protection layer may be formed on the laminate in a region which has a temperature in excess of 300° C. and less than 500° C. when the temperature control by means of the heater is performed (i.e., a region having an operating temperature of more than 300° C. and less than 500° C.)

According to this gas sensor element, since the porous protection layer is not formed in a region which is to have a temperature of 300° C. or less, as compared with the conventional gas sensor element having the porous protection layer formed in a region which is to have a temperature of 200° C. or higher, the area of formation of the porous protection layer can be reduced, along with power consumption, and standby time until initiation of detection. Furthermore, since the porous protection layer is formed in a region which is to have a temperature in excess of 300° C. and less than 500° C., resistance to adhesion of water is improved, whereby, even in use in such an environment that the amount of adhesion of water is much greater than in a conventional environment, the occurrence of cracking can be restrained.

A gas sensor of the present invention comprises a sensor element for detecting the concentration of a particular gas component in gas to be measured, and a housing for holding the sensor element therein and is characterized in that the sensor element is the above-mentioned gas sensor element.

According to the present invention, it is possible to reduce power consumption in heating the gas sensor element having the porous protection layer by the heater and standby time until initiation of detection, and to restrain occurrence of cracking as a result of adhesion of water to a solid electrolyte body.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

An embodiment of the present invention will next be described.

Figure 1:
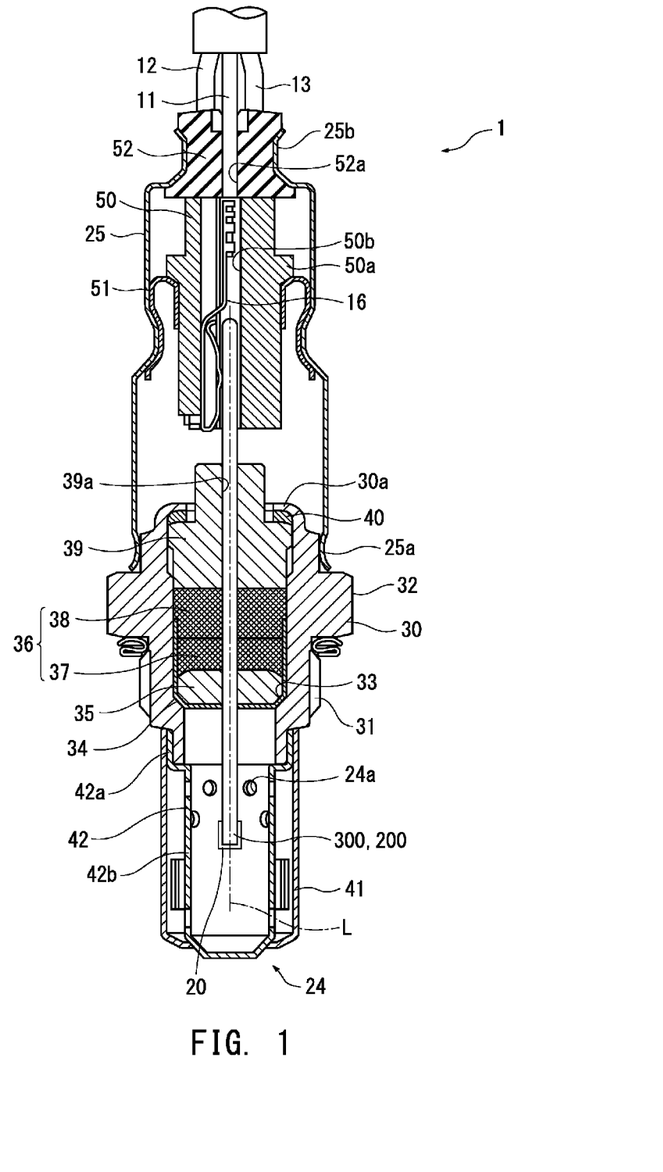
FIG. 1 is a longitudinal sectional view showing a gas sensor (oxygen sensor) according to an embodiment of the present invention.
Figure 2:
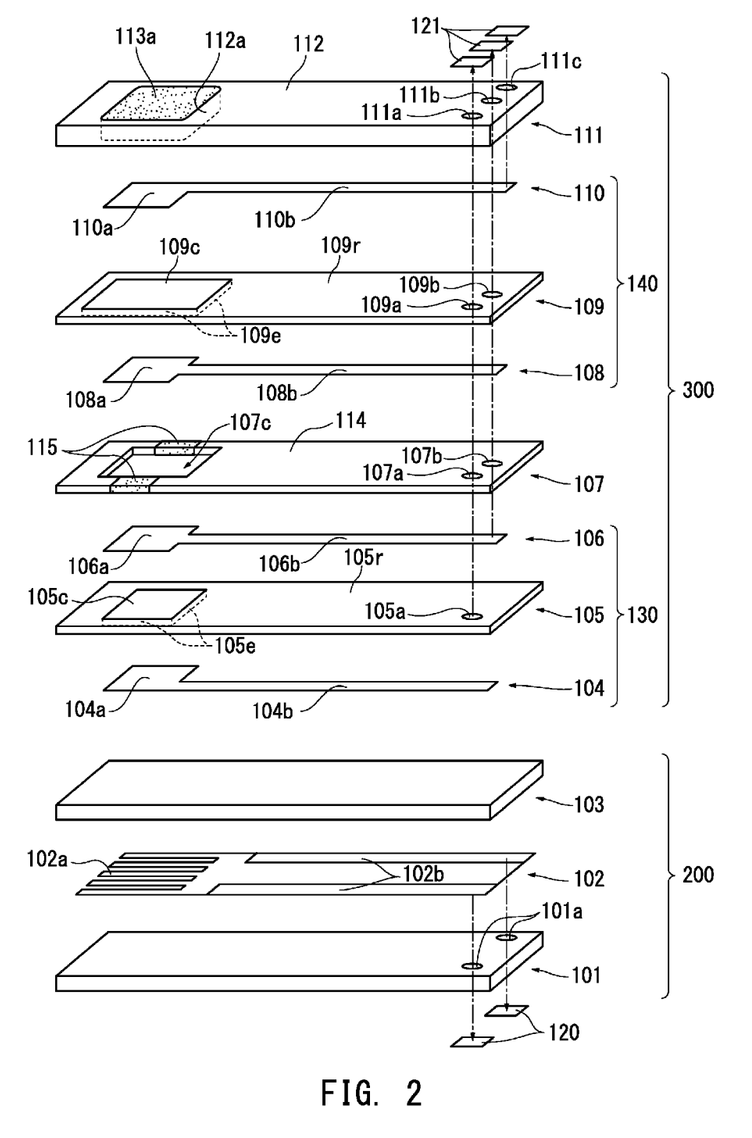
FIG. 2 is a schematic exploded perspective view showing a detecting element section and a heater section.
Figure 3:
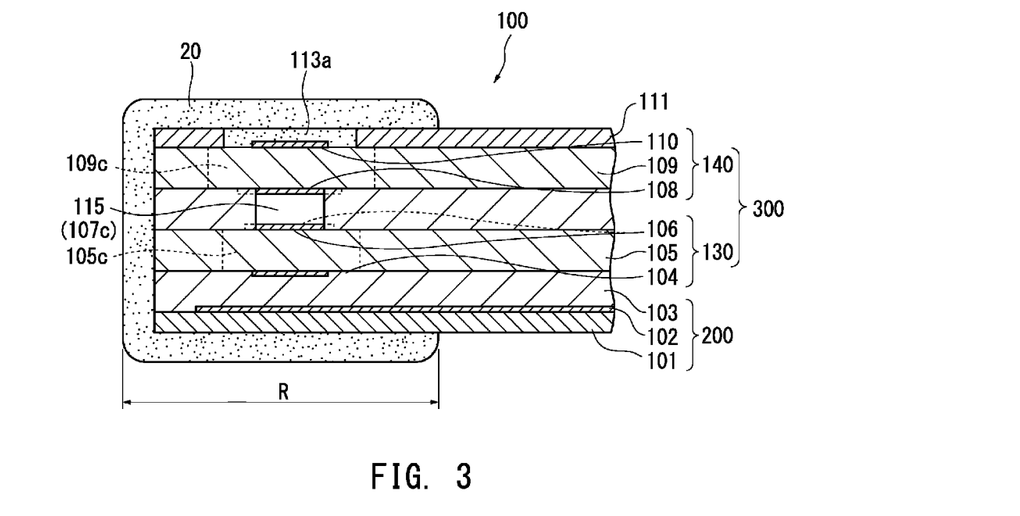
FIG. 3 is an enlarged fragmentary sectional view showing a forward end portion of a gas sensor element of FIG. 1.

FIG. 1 is a sectional view of a gas sensor (oxygen sensor) 1 according to the embodiment taken longitudinally (along an axis L); FIG. 2 is a schematic exploded perspective view showing a detecting element section 300 and a heater section 200; FIG. 3 is a sectional view of a gas sensor element 100 taken along the axis L.

As shown in FIG. 1, the gas sensor 1 includes the gas sensor element 100 composed of the detecting element section 300 and the heater section 200 laminated on the detecting element section 300; a metallic shell (corresponding to the "housing" appearing in claims) 30 for holding the gas sensor element 100, etc., therein; and a protector 24 attached to a forward end portion of the metallic shell 30. The gas sensor element 100 is disposed in such a manner as to extend along the axis L (in the longitudinal direction).

As shown in FIG. 2, the heater section 200 includes a first substrate 101 and a second substrate 103, which predominantly contain alumina, and a heat-generating element 102, which is sandwiched between the first substrate 101 and the second substrate 103 and predominantly contains platinum. The heat-generating element 102 has a heat-generating portion 102*a* located at the forward end thereof and a pair of heater lead portions 102*b* extending from the heat-generating portion 102*a* along the longitudinal direction of the first substrate 101. The ends of the heater lead portions 102*b* are electrically connected to corresponding heater-side pads 120 through conductors formed in heater-side through holes 101*a* provided in the first substrate 101.

A laminate of the first substrate 101 and the second substrate 103 corresponds to the "insulator" appearing in claims. Also, the heat-generating portion 102*a* corresponds to the "heater" appearing in claims.

The detecting element section 300 includes an oxygen concentration detecting cell 130 and an oxygen pump cell 140. The oxygen concentration detecting cell 130 includes a first solid electrolyte body 105*c*, and a reference electrode 104 and a detecting electrode 106, which are formed on the respective opposite sides of the first solid electrolyte body 105*c*.

Meanwhile, the first solid electrolyte body 105*c* has a generally rectangular plate-like shape, and a first support member 105*r* surrounds four end surfaces 105*e* in parallel with the direction of lamination of the first solid electrolyte body 105*c*. The first support member 105*r* incorporates the first solid electrolyte body 105*c* in a forward end portion thereof. The first support member 105*r* and the first solid electrolyte body 105*c* constitute a first layer 105, and the first layer 105 extends in the longitudinal direction and has the same dimensions as those of a protection layer 111, which will be described later, etc.

The reference electrode 104 is composed of a reference electrode portion 104a and a first lead portion 104b extending from the reference electrode portion 104a along the longitudinal direction of the first layer 105. The detecting electrode 106 is composed of a detecting electrode portion 106a and a second lead portion 106b extending from the detecting electrode portion 106a along the longitudinal direction of the first layer 105.

The end of the first lead portion 104b is electrically connected to a corresponding detecting-element-side pad 121 through conductors formed respectively in a first through hole 105a provided in the first layer 105 (first support member 105r), a second through hole 107a provided in an insulating layer 107 to be described later, a fourth through hole 109a provided in a second layer 109 (second support member 109r), and a sixth through hole 111a provided in the protection layer 111. The end of the second lead portion 106b is electrically connected to a corresponding detecting-element-side pad 121 through conductors formed respectively in a third through hole 107b provided in the insulating layer 107 to be described later, a fifth through hole 109b provided in the second support member 109r, and a seventh through hole 111b provided in the protection layer 111.

The oxygen pump cell 140 includes a second solid electrolyte body 109c, and an inner first pump electrode 108 and an outer first pump electrode 110, which are formed on respective opposite sides of the second solid electrolyte body 109c.

Meanwhile, the second solid electrolyte body 109c has a generally rectangular plate-like shape, and a second support member 109r surrounds four end surfaces 109e in parallel with the direction of lamination of the second solid electrolyte body 109c. The second support member 109r incorporates the second solid electrolyte body 109c in a forward end portion thereof. The second support member 109r and the second solid electrolyte body 109c constitute a second layer 109, and the second layer 109 extends in the longitudinal direction and has the same dimensions as those of the protection layer 111, which will be described later, etc. In the present embodiment, the second solid electrolyte body 109c is smaller in planar dimensions than the first solid electrolyte body 105c.

The inner first pump electrode 108 includes an inner first pump electrode portion 108a and a third lead portion 108b extending from the inner first pump electrode portion 108a along the longitudinal direction of the second layer 109. The outer first pump electrode 110 includes an outer first pump electrode portion 110a and a fourth lead portion 110b extending from the outer first pump electrode portion 110a along the longitudinal direction of the second layer 109.

The first support member 105r and the second support member 109r correspond to the "dense insulating member" appearing in claims. The term "dense" means, for example, such a density as not to allow passage of water and air.

The end of the third lead portion 108b is electrically connected to a corresponding detecting-element-side pad 121 through conductors formed respectively in the fifth through hole 109b provided in the second layer 109 (second support member 109r) and the seventh through hole 111b provided in the protection layer 111. The end of the fourth lead portion 110b is electrically connected to a corresponding detecting-element-side pad 121 through conductor formed in an eighth through hole 111c provided in the protection layer 111, which will be described later. The second lead portion 106b and the third lead portion 108b have the same electric potential.

The first solid electrolyte body 105c and the second solid electrolyte body 109c are partially-stabilized-zirconia sintered bodies which are formed by adding yttria ($Y_2O_3$) or calcia (CaO) as a stabilizer to zirconia ($ZrO_2$).

The heat-generating element 102, the reference electrode 104, the detecting electrode 106, the inner first pump electrode 108, the outer first pump electrode 110, the heater-side pads 120, and the detecting-element-side pads 121 can be formed of a platinum group element. Platinum group elements which are preferred for forming these components include Pt, Rh, and Pd. These elements can be used singly or in combination.

In view of heat resistance and resistance to oxidation, preferably, Pt is predominantly used to form the heat-generating element 102, the reference electrode 104, the detecting electrode 106, the inner first pump electrode 108, the outer first pump electrode 110, the heater-side pads 120, and the detecting-element-side pads 121. Furthermore, preferably, the heat-generating element 102, the reference electrode 104, the detecting electrode 106, the inner first pump electrode 108, the outer first pump electrode 110, the heater-side pads 120, and the detecting-element-side pads 121 contain a ceramic component in addition to a main component of a platinum group element(s). In view of attachment in a fixed condition, preferably, the ceramic component is similar to a material which is predominantly contained in a counterpart of lamination (e.g., a main component of the first solid electrolyte body 105c and the second solid electrolyte body 109c).

The insulating layer 107 is formed between the oxygen pump cell 140 and the oxygen concentration detecting cell 130. The insulating layer 107 includes an insulation portion 114 and a diffusion controlling portion 115. The insulation portion 114 of the insulating layer 107 has a hollow gas detecting chamber 107c formed at a position corresponding to the detecting electrode portion 106a and the inner first pump electrode portion 108a. The gas detecting chamber 107c communicates with the ambient atmosphere along the lateral direction of the insulating layer 107. In the communication region of the insulating layer 107, the diffusion controlling portion 115 is disposed so as to establish gas diffusion at a predetermined flow rate between the ambient atmosphere and the gas detecting chamber 107c.

No particular limitation is imposed on the first support member 105r, the second support member 109r, the insulation portion 114, and a reinforcement portion 112 to be described later, so long as these members are of an electrically insulative ceramic sintered body. Examples of such a ceramic sintered body include oxide ceramics such as alumina and mullite.

The diffusion controlling portion 115 and an electrode protection portion 113a to be described later are porous bodies formed of ceramic such as alumina. The diffusion controlling portion 115 controls the flow rate of gas to be detected when the gas flows into the gas detecting chamber 107c.

The protection layer 111 is formed on the surface of the second layer 109 such that the outer first pump electrode 110 is sandwiched therebetween. The protection layer 111 includes the porous electrode protection portion 113a, which covers the outer first pump electrode portion 110a for protecting the outer first pump electrode portion 110a from poisoning, and the reinforcement portion 112, which covers the fourth lead portion 110b and supports the electrode protection portion 113a. Meanwhile, the electrode protection portion 113a has a generally rectangular plate-like shape, and the reinforcement portion 112 surrounds four end surfaces in parallel with the direction of lamination of the electrode protection portion 113a. The reinforcement portion 112 incorporates the electrode protection portion 113a in a forward end portion thereof.

In the present embodiment, the electrode protection portion 113a is smaller in planar dimensions than the second solid electrolyte body 109c and is disposed inside the second solid electrolyte body 109c with respect to the lateral and longitudinal directions.

The gas sensor element 100 of the present embodiment corresponds to an oxygen sensor element which functions as follows: the direction and magnitude of current flowing between the electrodes of the oxygen pump cell 140 are adjusted such that voltage (electromotive force) generated between the electrodes of the oxygen concentration detecting cell 130 has a predetermined value (e.g., 450 mV), and the oxygen concentration in gas to be measured is linearly detected according to current which flows in the oxygen pump cell 140.

Also, the gas sensor element 100 of the present embodiment intermittently measures impedance (resistance) Rpvs of the first solid electrolyte body 105c of the oxygen concentration detecting cell 130 and feeds back, on the basis of the impedance, the condition of the gas sensor element 100 being heated by the heater (heat-generating portion) 102a.

Thus, the oxygen concentration detecting cell 130 which is subjected to temperature control by means of the heater 102a corresponds to the "cell-to-be-controlled" appearing in claims. Also, a target control temperature of the oxygen concentration detecting cell 130 in temperature control by means of the heater 102a corresponds to a temperature converted from impedance of the first solid electrolyte body 105c, and the target control temperature is set at 600° C. to 830° C.

Referring back to FIG. 1, the metallic shell 30 is made of SUS430 and includes an externally threaded portion 31 adapted to mount the gas sensor to an exhaust pipe, and a hexagonal portion 32 to which a mounting tool is fitted in mounting the gas sensor. The metallic shell 30 further includes a shell-side stepped portion 33, which projects radially inward. The shell-side stepped portion 33 supports a metal holder 34 for holding the gas sensor element 100. The metal holder 34 holds therein a ceramic holder 35 and talc 36 disposed in this order in the rearward direction. The talc 36 is composed of a first talc 37 disposed within the metal holder 34, and a second talc 38 disposed within the metal holder 34 and outside the rear end of the metal holder 34. The first talc 37 is compressively charged into the metal holder 34, thereby fixing the gas sensor element 100 in relation to the metal holder 34. Also, the second talc 38 is compressively charged into the metallic shell 30, thereby ensuring a seal between the outer surface of the gas sensor element 100 and the inner surface of the metallic shell 30. A sleeve 39 made of alumina is disposed on the rear side of the second talc 38. The sleeve 39 is formed into a multi-stepped cylindrical shape and has an axial hole 39a extending along the axial line. The gas sensor element 100 extends through the axial hole 39a. A rear-end crimp portion 30a of the metallic shell 30 is bent inward, thereby pressing the sleeve 39 toward the forward end of the metallic shell 30 through a ring member 40 made of stainless steel.

A protector 24 made of metal and having a plurality of gas intake holes 24a is welded to the outer circumferential surface of a forward end portion of the metallic shell 30 and covers a forward end portion of the gas sensor element 100 projecting from the forward end of the metallic shell 30. The protector 24 has a dual structure consisting of a closed-bottomed cylindrical outer protector 41 having a fixed outside diameter and a closed-bottomed cylindrical inner protector 42 disposed within the outer protector 41 and formed such that its rear end portion 42a is greater in outside diameter than its forward portion 42b.

Meanwhile, a forward end portion of an outer tube 25 made of SUS430 is fitted to a rear end portion of the metallic shell 30. The outer tube 25 is fixed to the metallic shell 30 by crimping and then laser-welding its diameter-expanded forward portion 25a to the metallic shell 30. A separator 50 is disposed within a rear portion of the outer tube 25. A holding member 51 intervenes between the separator 50 and the outer tube 25. The holding member 51 is engaged with a flange portion 50a of the separator 50, which will be described later, and is fixed between the outer tube 25 and the separator 50 by crimping the same and the outer tube 25 together.

The separator 50 has a through hole 50b extending therethrough between its forward end and rear end for allowing insertion of lead wires 11 to 15 associated with the detecting element section 300 and the heater section 200 (the lead wires 14 and 15 are not shown). The through hole 50b accommodates connection terminals 16 for connecting the lead wires 11 to 15 to the detecting-element-side pads 121 of the detecting element section 300 and to the heater-side pads 120 of the heater section 200. The lead wires 11 to 15 are connected to unillustrated external connectors. Electrical signals are transmitted between the lead wires 11 to 15 and external equipment such as ECU through the connectors. Although unillustrated in detail, the lead wires 11 to 15 have a structure in which a conductor is covered with an insulation film made of resin.

Furthermore, a substantially circular columnar rubber cap 52 is disposed on the rear side of the separator 50, for closing a rear end opening 25b of the outer tube 25. The rubber cap 52 fitted into the outer tube 25 is fixed to the outer tube 25 as follows: in a state in which the rubber cap 52 is fitted into the rear end of the outer tube 25, the outer tube 25 is crimped radially inward along its outer circumference. The rubber cap 52 also has through holes 52a extending therethrough between its forward end and rear end for allowing the lead wires 11 to 15 to extend through the respective through holes 52a.

Next will be described a porous protection layer 20, which is a feature of the present invention. As shown in FIG. 1, the porous protection layer 20 completely surrounds the entire perimeter (four surfaces; i.e., front and back surfaces and two side surfaces) of a forward end portion of the gas sensor element 100.

FIG. 3 is an enlarged fragmentary sectional view showing a forward end portion of the gas sensor element 100 in FIG. 1. The porous protection layer 20 is formed on a surface of the laminate of the detecting element section 300 and the heater section 200 in a region R which extends rearward from the forward end surface of the gas sensor element 100 along the axial line L and which has a temperature of 500° C. or higher in the course of use of the gas sensor element 100, and is not formed in a region which has a temperature of 300° C. or lower in the course of use.

All end surfaces 105e and 109e (see FIG. 2) of the first solid electrolyte body 105c and the second solid electrolyte body 109c are surrounded by dense insulating members; i.e., the first support member 105r and the second support member 109r, respectively. Thus, the end surfaces 105e and 109e are not exposed to the exterior of the gas sensor element 100, and, even when a water droplet comes into direct contact with (adheres to) a high-temperature portion having a temperature in excess of 200° C. and equal to or less than 300° C. of the gas sensor element 100, excessive thermal stress is not imposed on the first solid electrolyte body 105c and the second solid electrolyte body 109c, thereby restraining occurrence of cracking.

Therefore, by means of the porous protection layer 20 being formed in the higher-temperature region R which extends rearward from the forward end portion of the gas sensor element 100 and is to have a temperature of 500° C. or higher, the area of formation of the porous protection layer 20 can be reduced without involvement of occurrence of cracking in the solid electrolyte bodies 105c and 109c, and heat capacity of the porous protection layer 20 and, in turn, heat capacity of the gas sensor element 100 can be reduced. As a result, there can be reduced power consumption in heating the gas sensor element 100 by the heater 102a, and standby time until initiation of detection.

In the present embodiment, the region R extends, along the axial line L, rearward of a region which overlies the reference electrode portion 104a, the detecting electrode portion 106a, the inner first pump electrode portion 108a, and the outer first pump electrode portion 110a.

The porous protection layer 20 can be formed by joining together, through firing or the like, particles of ceramic selected singly or in combination from the group consisting of alumina, spinel, zirconia, mullite, zircon, and cordierite. By sintering a slurry which contains the particles, pores can be formed in the matrix of a film; however, by sintering a slurry which contains the particles and a burning-off-type pore-forming material, the pore-forming material burns off to become pores. Examples of the usable pore-forming material include carbon, resin beads, and organic or inorganic binder particles.

The thickness of the porous protection layer 20 is preferably 50 μm to 800 μm, more preferably 550 μm to 650 μm.

Figure 4:
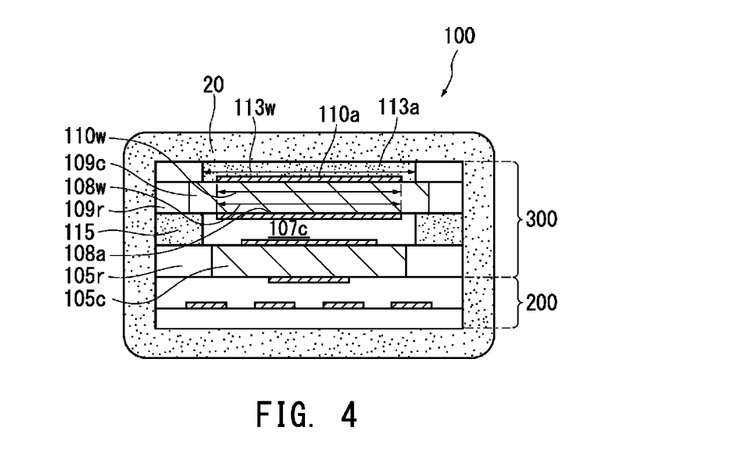
FIG. 4 is a schematic sectional view of the gas sensor element taken orthogonally to the axial direction.

FIG. 4 is a schematic sectional view of the gas sensor element 100 which includes the porous protection layer 20, taken orthogonally to the axial line L (taken along the lateral direction).

In the present embodiment, a width 108w of the inner first pump electrode portion 108a is smaller than a width 113w of the electrode protection portion 113a. Also, a width 110w of the outer first pump electrode portion 110a is equal to the width 108w of the inner first pump electrode portion 108a.

Furthermore, the surface of the outer first pump electrode portion 110a is covered directly with the electrode protection portion 113a.

As mentioned above, through employment of the dimensional relation 110w≤113w, the dimension 110w can be reliably rendered smaller than the dimension 113w.

As a result, the outer first pump electrode portion 110a can be reliably disposed laterally inside the electrode protection portion 113a, and, even in the case where the outer first pump electrode portion 110a and the electrode protection portion 113a are in direct contact with each other, there can be eliminated a problem in that the outer first pump electrode portion 110a breaks as a result of existence thereof at a boundary 112a (FIG. 2) between the electrode protection portion 113a and the reinforcement portion 112 where a difference in level exists. Also, there is no need to provide a buffer layer between the outer first pump electrode portion 110a and the electrode protection portion 113a for eliminating the difference in level; thus, as compared with the case of provision of the buffer layer, the transmittance of gas from the ambient atmosphere through the electrode protection portion 113a can be improved.

As shown in FIG. 3, the inner first pump electrode portion 108a is also smaller in length than the electrode protection portion 113a with respect to the direction of the axial line L. Also, the length of the outer first pump electrode portion 110a is equal to the length of the inner first pump electrode portion 108a. Thus, even in the case where the outer first pump electrode portion 110a and the electrode protection portion 113a are in direct contact with each other, there can be more reliably eliminated a problem in that the outer first pump electrode portion 110a breaks as a result of existence thereof at a boundary 112a (FIG. 2) between the electrode protection portion 113a and the reinforcement portion 112 where a difference in level exists.

Also, in the present embodiment, the gas detecting chamber 107c communicates with the ambient atmosphere through the diffusion controlling portion 115 along the width direction of the gas sensor element 100. Thus, as compared with the case where the gas detecting chamber 107c communicates with the ambient atmosphere, for example, through a through hole extending through layers in the direction of lamination, the transmittance of gas from the ambient atmosphere can be improved.

The gas sensor element 100 according to the present embodiment of the present invention can be manufactured, for example, as follows.

First, a green heater section 200 is formed in the following manner. A paste prepared from material powder of alumina or the like, binder, plasticizer, etc., is formed into a sheet by the doctor blade process or the like, followed by drying to yield a green sheet; then, the green sheet is cut into a predetermined size, thereby yielding a green first substrate 101 and a green second substrate 103. Then, a paste prepared from material powder of Pt or the like, binder, plasticizer, etc., is screen-printed on the green first substrate 101, followed by drying to yield a green heat-generating element 102. Subsequently, the green first substrate 101 and the green second substrate 103 are laminated together such that the green heat-generating element 102 is sandwiched therebetween.

Similarly, a rectangular piece is cut out from a forward end portion of the green first support member 105r formed of an alumina green sheet, and a green first solid electrolyte body 105c formed of a partially-stabilized-zirconia green sheet is fitted into the formed rectangular hole. Then, a green reference electrode 104 and a green detecting electrode 106 are paste-printed onto respective opposite sides of the green first layer 105, thereby yielding a green oxygen concentration detecting cell 130. Furthermore, a green insulation portion 114 and a green diffusion controlling portion 115 are paste-printed onto the surface of the green first layer 105 located toward the green detecting electrode 106.

Similarly, a rectangular piece is cut out from a forward end portion of the green second support member 109r formed of an alumina green sheet, and a green second solid electrolyte body 109c formed of a partially-stabilized-zirconia green sheet is fitted into the formed rectangular hole. Then, a green inner first pump electrode 108 and a green outer first pump electrode 110 are paste-printed onto respective opposite sides of the green second layer 109, thereby yielding a green oxygen pump cell 140.

Then, the green heater section 200, the green oxygen concentration detecting cell 130, and the green oxygen pump cell 140 are laminated, followed by firing to manufacture the gas sensor element 100.

The present invention is not limited to the above-described embodiment, but is applicable to any gas sensor (gas sensor element) which has a detecting element section composed of one or more cells, and a heater section, as well as to the oxygen sensor (oxygen sensor element) of the present embodiment. However, application of the present invention is not limited thereto, and the present invention may encompass various modifications and equivalents thereof without departing from the gist and scope of the invention. For example, the present invention may be applied to an $NO_x$ sensor ($NO_x$ sensor element) for detecting the $NO_x$ concentration of gas to be measured and an HC sensor (HC sensor element) for detecting the HC concentration of gas to be measured.

In the above-described embodiment, the porous protection layer 20 is formed of ceramic particles; however, the porous protection layer 20 may be formed of a mixture of ceramic particles and ceramic fiber.

In the above-described embodiment, the sheet-like green first solid electrolyte body 105c is fitted into a cutout hole of the sheet-like green first support member 105r, followed by firing to cover the end surfaces of the first solid electrolyte body 105c with the first support member 105r (the same also applies to the second solid electrolyte body 109c). However, a paste which is to become a dense insulating member may be applied to the green first solid electrolyte body 105c (green second solid electrolyte body 109c), followed by firing.

Dripping Test

The plate-like gas sensor element (oxygen sensor element) 100 shown in FIGS. 1 to 4 was prepared as an "Example" such that the porous protection layer 20 was provided. The plate-like gas sensor element (oxygen sensor element) 100 was prepared as a "Reference Example" such that a porous protection layer 1400 was not provided. Furthermore, a gas sensor element (oxygen sensor element) 1000 having a sectional structure shown in FIG. 6 was prepared as a "Comparative Example" such that the porous protection layer 1400 was not provided. The gas sensor element 1000 of the Comparative Example has a structure similar to that of the gas sensor element 100 except that the solid electrolyte bodies 105c and 109c are not surrounded by the first support member 105r and the second support member 109r, respectively, and are laminated with the other layers 107 and 111 while having the same dimensions as those of the layers 107 and 111, and the end surfaces of the solid electrolyte bodies 105c and 109c are exposed to the exterior of the gas sensor element 1000.

Each gas sensor element 100 or 1000 was held horizontally with one side surface thereof in parallel with the direction of lamination facing upward. Microsyringes were disposed immediately above the side surface at positions located above and along the axial line of the side surface for dripping a water droplet. Next, electricity was applied to the heaters 102a to heat the gas sensor elements such that the oxygen concentration detecting cells 130 had a target control temperature of 830° C.; then, a water droplet was dripped on the above-mentioned heated side surface at the axial positions to observe whether or not cracking occurs.

Dripping was performed on the three gas sensor elements. The heated side surface was measured for temperature along the axial line thereof by means of thermography. A water droplet was dripped on the heated side surface at its center (in the thickness direction) at eight axial positions which had eight respective temperatures of 100° C. to 720° C. shown in Table 1, as well as at an axial position having a highest temperature of 830° C. Dripping was performed sequentially from the axial positions having a temperature of 100° C. (from the rearmost axial positions). As shown in Table 1, the amount of a water droplet to be dripped was 2.0 μl or 3.0 μl, and dripping was repeated 20 times at a water droplet amount of 2.0 μl or 3.0 μl.

At each position (each temperature) up to the position having the highest temperature (830°), the side surfaces were observed and checked by penetrant inspection (red check) at positions of dripping for occurrence and degree of cracking after completion of the dripping.

Table 1 Shows the Results of the Test.

In Table 1, the letter "A" indicates that the gas sensor element has been free from cracking, and the letter "F" indicates that the gas sensor has suffered cracking.

TABLE 1

| Temperature (° C.) | 100 | 200 | 250 | 300 | 400 | 500 | 600 | 720 | 830 | Porous protection layer | Amount of dripping (μL) | Dense insulating member |
|---|---|---|---|---|---|---|---|---|---|---|---|---|
| Example | A | A | A | A | A | A | A | A | A | Provided | 3.0 | Provided |
| Reference | A | A | A | A | A | F | F | F | F | Not provided | 3.0 | Provided |
| Example | A | A | A | A | A | A | F | F | F | provided | 2.0 | |
| Comparative Example | A | A | A | F | F | F | F | F | F | Not provided | 2.0 | Not provided |

As is apparent from Table 1, in comparison of test results at an amount of dripping of 2.0 μL between Reference Example and Comparative Example, the gas sensor element of Comparative Example in which the end surfaces of the solid electrolyte bodies are exposed at the side surfaces thereof has suffered cracking in an area extending from the forward end portion of the gas sensor element to a region having a temperature of 300° C. or higher.

By contrast, the gas sensor element of Reference Example in which all end surfaces of the solid electrolyte bodies are covered with the respective dense insulating members has been free from cracking in an area extending from the forward end portion of the gas sensor element to a region having a temperature of 500° C. or less.

In a dripping test at an amount of dripping of 3.0 μL, which is severer than in the conventional dripping test, the gas sensor element of Reference Example has been free from cracking in an area extending from the forward end portion of the gas sensor element to a region having a temperature of 400° C., but has suffered cracking in a region having a temperature of 500° C.

In a dripping test at an amount of dripping of 3.0 μL, the gas sensor element of Example has been free from cracking in the entire region having test temperatures.

Power Consumption Evaluation Test

There were prepared plate-like gas sensor elements (oxygen sensor elements) 100 shown in FIGS. 1 through 4 and differed in axial length of the porous protection layer 20. Specifically, when the gas sensor element 100 was heated through application of electricity to the heater 102a such that the oxygen concentration detecting cell 130 had the target control temperature of 830° C., the side surface of the gas sensor element 100 was measured for temperature at the position of the rear end of the porous protection layer 20, and the measured temperature was employed as an index of the axial length of the porous protection layer 20.

Figure 5:
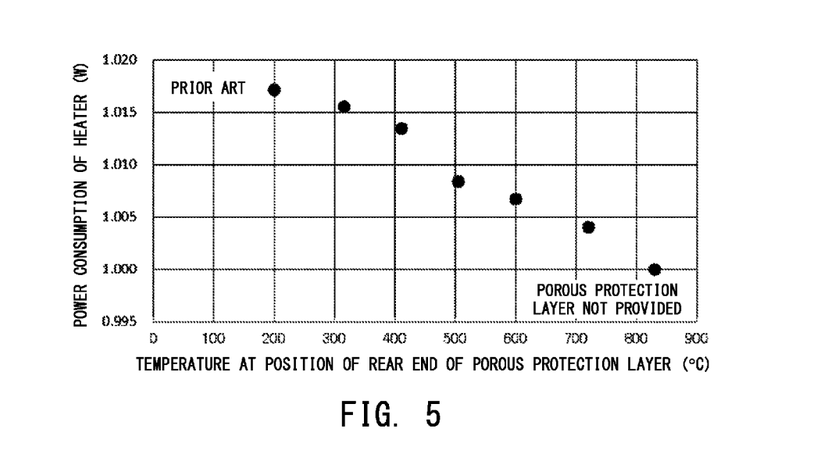
FIG. 5 is a diagram showing the relation between the length of a porous protection layer and power consumption of a heater.

For example, "200° C." in FIG. 5 indicates that the porous protection layer 20 is formed from the forward end of the gas sensor element 100 to a position where the temperature becomes 200° C. when the gas sensor element 100 is heated. Therefore, in FIG. 5, the higher the temperature, the shorter the length of the porous protection layer 20. In the case where the porous protection layer 20 is not formed, the highest attainment temperature of the gas sensor element 100; specifically, 830° C., is employed.

Electricity was applied to the heaters 102a of the gas sensor elements 100 which differed in the length of the porous protection layer 20. After the elapse of three minutes subsequent to the stabilization of the above-mentioned impedance (resistance) Rpvs, the power consumption (W) of the heaters 102a was obtained from voltage and current applied to the heaters 102a. The power consumption of the heater is taken as "1" for the case where the porous protection layer 20 is not formed (830° C.), and the power consumption of the heaters in question is represented by a relative value in relation to that in the case where the porous protection layer 20 is not formed (830° C.)

FIG. 5 shows the obtained data. As is apparent from FIG. 5, the higher the temperature at the position of the rear end of the porous protection layer, the lower the power consumption of the heater. In other words, the shorter the length of the porous protection layer, the lower the power consumption of the heater. However, the power consumption of the heater first decreases greatly between the case where the porous protection layer extends from the forward end of the gas sensor element to the position where the temperature becomes 400° C. and the case where the porous protection layer extends from the forward end of the gas sensor element to the position where the temperature becomes 500° C. Therefore, the power consumption of the heater was determined to have decreased sufficiently when the porous protection layer was formed to extend from the forward end of the gas sensor element to a region having a temperature of 500° C. or higher.

The above-mentioned test results have revealed that, since the gas sensor element of Example is such that all end surfaces of the solid electrolyte bodies are covered with the respective dense insulating members, the end surfaces are not exposed to the exterior of the gas sensor element; accordingly, even when a water droplet comes into direct contact with (adheres to) a portion of the gas sensor element which is to have a temperature in excess of 200° C. and equal to or less than 300° C., the solid electrolyte bodies are free from imposition of excessive thermal stress thereon, whereby the occurrence of cracking is restrained.

Since the porous protection layer is formed at least in a higher-temperature region which extends from the forward end portion of the gas sensor element and has a temperature of 500° C. or higher, and is not formed in a region which is to have a temperature of 300° C. or less, as compared with the conventional gas sensor element having the porous protection layer formed in the entire region which is to have a temperature of 200° C. or higher, power consumption in heating the gas sensor element by the heater, and standby time until initiation of detection can be reduced.

Also, by means of the porous protection layer being not formed on the laminate in a region which is to have a temperature less than 500° C. in the course of temperature control by means of the heater, while the occurrence of cracking is restrained, power consumption, and standby time until initiation of detection can be further reduced.

Also, by means of the porous protection layer being formed on the laminate in a region which has a temperature in excess of 300° C. and less than 500° C. in the course of temperature control by means of the heater, and being not formed in a region which has a temperature equal to or less than 300° C., as compared with the conventional gas sensor element having the porous protection layer formed in the entire region which is to have a temperature of 200° C. or higher, the area of formation of the porous protection layer can be reduced, and power consumption, and standby time until initiation of detection can be reduced. Furthermore, since the porous protection layer is formed in a region which is to have a temperature in excess of 300° C. and less than 500° C., resistance to adhesion of water is improved, whereby, even in use in such an environment that the amount of adhesion of water is greatly increased as compared with a conventional environment, the occurrence of cracking can be restrained.

DESCRIPTION OF REFERENCE NUMERALS

1: gas sensor
20: porous protection layer
30: housing
104, 105, 108, 110: paired electrodes
105c: first solid electrolyte body
107c: gas detecting chamber
109c: second solid electrolyte body
105e, 109e: end surface of solid electrolyte body
105r, 109r: dense insulating member
100: gas sensor element
102a: heater
113a: electrode protection portion
130, 140: cell
130: cell-to-be-controlled
200: heater section
300: detecting element section
L: axial line

What is claimed is:

1. A gas sensor element comprising:
  a heater section including an insulator and a heater in the insulator; and
  a detecting element section laminated with the heater section to form a laminate, the laminate having a region having an operating temperature of 500° C. or higher and a region having an operating temperature of 300° C. and lower, the detecting element section including:
    one or more cells, each of the one or more cells including a solid electrolyte body having side surfaces parallel to a lamination direction, and a pair of electrodes disposed on each solid electrolyte body, a temperature of a cell-to-be-controlled of the one or more cells controlled by the heater to a target control temperature of 600° C. to 830° C.; and
    a dense insulating member covering the side surfaces of each solid electrolyte body; and
  a porous protection layer formed on the laminate from a forward end to the region having the operating temperature of 500° C. or higher, and the porous protection layer not formed on the laminate in the region having the operating temperature of 300° C. and lower.

2. The gas sensor element according to claim 1, wherein the laminate further includes a region having an operating temperature of less than 500° C., and wherein the porous protection layer is not formed on the laminate in the region having the operating temperature of less than 500° C.

3. The gas sensor element according to claim 1, wherein the laminate further includes a region having an operating temperature of more than 300° C. and less than 500° C., and wherein the porous protection layer is formed on the laminate in the region having the operating temperature of more than 300° C. and less than 500° C.

4. A gas sensor comprising:
   the gas sensor element according to claim 1 for detecting a concentration of a particular gas component in gas to be measured, and
   a housing for holding the gas sensor element therein.

5. A gas sensor comprising:
   the gas sensor element according to claim 2 for detecting a concentration of a particular gas component in gas to be measured, and
   a housing for holding the gas sensor element therein.

6. A gas sensor comprising:
   the gas sensor element according to claim 3 for detecting a concentration of a particular gas component in gas to be measured, and
   a housing for holding the gas sensor element therein.

* * * * *